United States Patent
Dieterle

(10) Patent No.: US 10,119,852 B2
(45) Date of Patent: Nov. 6, 2018

(54) ADJUSTMENT-FREE FILL LEVEL SENSOR

(71) Applicant: VEGA Grieshaber KG, Wolfach (DE)

(72) Inventor: Levin Dieterle, Wolfach (DE)

(73) Assignee: VEGA GRIESHABER KG, Wolfach (DE)

( * ) Notice: Subject to any disclaimer, the term of this patent is extended or adjusted under 35 U.S.C. 154(b) by 260 days.

(21) Appl. No.: 15/090,213

(22) Filed: Apr. 4, 2016

(65) Prior Publication Data

US 2016/0298994 A1    Oct. 13, 2016

(30) Foreign Application Priority Data

Apr. 7, 2015   (EP) .................................. 15 162 633

(51) Int. Cl.

| | |
|---|---|
| *G01F 23/00* | (2006.01) |
| *G01F 25/00* | (2006.01) |
| *G01F 23/26* | (2006.01) |
| *G01F 23/296* | (2006.01) |
| *G01F 23/24* | (2006.01) |
| *G01N 9/36* | (2006.01) |
| *G01N 15/08* | (2006.01) |
| *G01N 29/07* | (2006.01) |

(52) U.S. Cl.
CPC ...... *G01F 23/0069* (2013.01); *G01F 23/0061* (2013.01); *G01F 23/0076* (2013.01); *G01F 23/24* (2013.01); *G01F 23/263* (2013.01); *G01F 23/265* (2013.01); *G01F 23/268* (2013.01); *G01F 23/296* (2013.01); *G01F 23/2961* (2013.01); *G01F 23/2962* (2013.01); *G01F 25/0061* (2013.01); *G01N 9/36* (2013.01); *G01N 15/082* (2013.01); *G01N 29/07* (2013.01); *G01N 2291/02836* (2013.01); *G01N 2291/045* (2013.01)

(58) Field of Classification Search
CPC .. G01F 23/0061; G01F 23/0069; G01F 23/24; G01F 23/268; G01F 25/0061; G01F 23/246; G01N 15/082; G01N 9/36
See application file for complete search history.

(56) References Cited

U.S. PATENT DOCUMENTS

| | | | |
|---|---|---|---|
| 3,485,740 A | * | 12/1969 | Souza ..................... G01N 27/36 204/413 |
| 3,706,980 A | | 12/1972 | Maltby |
| 5,949,000 A | * | 9/1999 | Lindholm ................. B01L 3/04 374/139 |

(Continued)

FOREIGN PATENT DOCUMENTS

| | | |
|---|---|---|
| DE | 40 25 400 | 4/1992 |
| DE | 198 39 000 | 3/2000 |

(Continued)

*Primary Examiner* — Francis C Gray
(74) *Attorney, Agent, or Firm* — Fay Kaplun & Marcin, LLP

(57) ABSTRACT

A measuring instrument for detecting a fill level or a limit level of a medium, for example fill levels in containers or chambers, is provided. The measuring instrument includes a sensor unit, which takes at least two measurements at two different penetration depths in the medium. For this purpose, an arithmetic-logic unit makes calculations so as to distinguish complete covering of the sensor unit by a medium from adhesion of parts of the medium to the sensor unit, using the results of the measurements.

16 Claims, 3 Drawing Sheets

(56) References Cited

U.S. PATENT DOCUMENTS

| | | |
|---|---|---|
| 7,423,436 B2 | 9/2008 | Gundlach et al. |
| 9,459,132 B2* | 10/2016 | Fehrenbach .......... G01F 23/296 |
| 9,719,834 B2* | 8/2017 | Gruhler ............... G01F 23/2968 |
| 2008/0072667 A1 | 3/2008 | Mueller et al. |
| 2014/0290357 A1* | 10/2014 | Zhang .................. G01F 23/246 |
| | | 73/295 |

FOREIGN PATENT DOCUMENTS

| | | |
|---|---|---|
| DE | 103 28 296 | 1/2005 |
| DE | 10 2005 027 344 | 1/2007 |
| DE | 20 2011 107 423 | 1/2012 |
| DE | 10 2014 006 695 | 11/2014 |
| EP | 2 667 162 | 11/2013 |

\* cited by examiner

ADJUSTMENT-FREE FILL LEVEL SENSOR

REFERENCE TO RELATED APPLICATIONS

This application claims the benefit of the filing date of European Patent Application Serial No. 15 162 633.0 filed on 7 Apr. 2015, the disclosure of which is hereby incorporated herein by reference.

FIELD OF THE INVENTION

The invention relates to a measuring instrument for detecting a fill level or limit level of a medium, as well as to a method for detecting a fill level or limit level of a medium, to a program element and to a computer-readable medium.

BACKGROUND

Level sensors are used for example to measure the fill height or level of a medium in a container. Information regarding physical properties of the medium is generally not automatically available to the sensor. In particular, the permittivity or electrical conductivity may be of interest. The permittivity, also known as dielectric conductivity, specifies the "permeability" of a medium to electric fields. The electrical conductivity is inversely proportional to the electrical resistance.

However, during the operation of a system comprising a container containing a medium or comprising a fluid sensor in a chamber, it is possible for a certain amount of the medium to adhere to the sensor even though the level of the medium is below the sensor; in other words, the sensor is not immersed in the medium. In other cases, when the level falls, part of the medium may adhere to the container wall or to the housing, behind which the level sensor is located. This may occur in particular in highly viscous, in other words glutinous fluids, which also additionally have adhesive properties.

These situations may lead to incorrect measurements or imprecisions. One reason for this is that, under some circumstances, a sensor which has no information about the physical properties of the medium to be measured cannot distinguish between adhesion and being completely covered by the medium. This is the case in particular if the physical properties, to which the sensor is sensitive by virtue of the measuring principle thereof, are very pronounced in the adhering substance (for example a medium having high relative permittivity in the case of a capacitive sensor) and these physical properties are only slight in a medium completely covering the sensor.

A passive guard, in particular a guard electrode, may be used to solve this problem, so as to largely block out a region close to the surface, in which adhesion takes place, from the measurement region of the sensor.

DE 10 2005 027 344 A1 discloses distinguishing between different media using impedance spectroscopy, the impedance being measured as a function of the exciting frequency.

SUMMARY OF THE INVENTION

A first aspect of the invention relates to a measuring instrument for detecting a fill level or limit level of a medium, comprising a sensor unit, which is configured to take at least two measurements at two different penetration depths in the medium, and an arithmetic-logic unit or control unit, which is configured to distinguish complete covering of the sensor unit by a medium from adhesion of parts of the medium to the sensor unit, using the results of the at least two measurements. Preferably, one measurement measures a region close to the sensor surface, which is strongly influenced by an adhering medium. The other is a measurement which measures a volume region extending deeper into the space in front of the sensor surface. Thus, incorrect measurements or incorrect switching decisions due to adhesion by a medium may be prevented.

Media are for example fluids, such as liquids or mixed gas/liquid forms, such as supercritical fluids. The medium may also consist of mixtures of substances, such as suspensions, foams, mixtures, emulsions. However, bulk materials are also conceivable. The object of the measuring instrument is to detect these media so as to detect a fill level or limit level. In particular, the measuring instrument can detect the presence of the medium and/or the degree of covering, for example a fill level. It is also conceivable for the measuring instrument to be located in a multiply open or half-open chamber and for the measuring instrument to detect a medium therein. An example of a multiply open chamber is a pipe in which the presence of a fluid is to be detected.

Complete covering of the sensor unit by a medium differs from adhesion of parts of the medium in that the sensor unit is immersed in the medium if the sensor unit is completely covered. In other words, if the sensor unit is completely covered by a medium, the level of the medium is above the sensor unit. By contrast, adhesion of parts of the medium means that residues of the medium are adhering to the sensor unit even though the level of the medium is below the sensor unit. This may happen for example if at least some of the medium is drained from the container.

The medium often has adhesive properties specifically if it consists of a liquid or glutinous substance. This means that it can adhere to the sensor or to a surface behind which the sensor is located even though the majority of the medium has already been withdrawn. One example of this is a container having a falling level of a liquid which adheres to a container wall or to a surface behind which the measuring instrument is located or to the sensor itself.

Equally, damp and/or sticky bulk materials, such as sand, salt, animal feed (dry/wet) or muesli may leave behind adhesions on the container wall and sensor surface.

This effect is promoted by high-viscosity or very glutinous fluids. These subsequently wet a surface directly in front of the sensor unit and are thus detected by the sensor. Among other things, in this state the sensor unit takes at least two measurements. These may be two measurements at different depths in the medium surrounding the sensor, or else more than two measurements, in which case at least two depths should still be detected. The reason for this is that the equations to be solved include at least two unknowns. These are dependent both on at least one physical material property and on the thickness to which the sensor is covered by medium. If measurement curves are determined, these turn out differently depending on the thickness to which the sensor unit is covered by the medium and depending on the physical properties thereof. The sensor unit may now be pre-calibrated to optimise the functioning thereof for a medium. If the medium and thus the physical material properties change, different measurement curves are generally obtained, which would in that case suggest incorrect cover layer thicknesses (if only one measurement were taken). For this purpose, in the proposed sensor unit at least two measurements are taken at different depths in the medium. This provides at last two measurement values which can be substituted into the equations to determine the layer thickness and the at least one physical medium property. From this information calculated by the arithmetic-logic unit, it can now be deduced whether residues of the medium are adhering in whole or in part to the sensor unit or a surface in front of the sensor unit and the remainder of the medium has already been withdrawn at least in part from the container or chamber to be detected, or whether the sensor or the surface in front of the sensor is completely covered by the fluid. This prevents confusion between, on the one hand, adhesion by media having very pronounced physical properties (for example high relative permittivity) and, on the other hand, complete covering of the sensor unit or the surface in front of the sensor unit by the medium, which extends as a whole as far as the sensor unit or the surface in front of the sensor unit.

It may be an advantageous effect of the invention that the fill level measuring instrument determines the physical properties of the medium at every measurement, or, in other words, that an input into the device by the user, regarding the type of medium to be measured or the values of particular physical properties of the medium, such as permittivity or electrical conductivity, is not required. In addition, measurements can also be carried out more reliably, even if a certain amount of the filling material adheres to a sensor or to a container wall or another surface or even completely covers it. In addition, a switching point of a limit level sensor of the measuring device can be determined without having to take into account the physical material properties of the medium to be measured. This can make possible a more rapid reaction to the degree of covering of a sensor and to the change in a switching state of a limit level sensor. It may also be provided that the disclosed measuring instrument carries out temperature compensation by measuring at least one physical media property (assuming that the medium being measured has not changed), since changes in temperature lead to changes in the physical media properties and can thus change the respective measurement curves.

In one embodiment of the invention, the arithmetic-logic unit is further configured to determine physical material properties by evaluating the at least two measurements. Primarily, the arithmetic-logic unit is configured to determine covering thickness. For this purpose, a physical parameter from the equation system to be solved can be eliminated without explicitly calculating it, for example. However, it may also be calculated and stored on a storage unit, for example for further uses. It may also be conveyed via a transceiver unit to a central evaluation point, for example in safety-critical systems for verifying the medium or the relevant medium parameters.

In a further embodiment of the invention, the measuring instrument further comprises a passive guard or shield, which is configured to largely block out the adhesion from the volume region monitored by the first sensor element, and which is additionally configured to detect the influence of the covering and/or adhering medium as a second sensor element and to actively evaluate it by way of the arithmetic-logic unit.

In a further embodiment of the invention, the guard is a guard electrode which serves to improve the measurement in the case of an impedance measurement and to largely block out undesirable regions close to the surface from the volume region monitored by the first measuring electrode, and which is additionally configured to detect the influence of the covering and/or adhering medium as a second electrode and to actively evaluate it by way of the arithmetic-logic unit.

In a further embodiment of the invention, in addition to the at least two sensor elements the measuring instrument further comprises a passive guard, which is configured to largely limit the volume region monitored by the relevant sensor elements to the region located in front of the sensor surface, in other words the region influenced by the medium. In this way, influences due to the construction, brought about by the geometry of the sensor construction, can be minimised to the measurement result. The passive guard may be present in addition to the sensor elements, or else at least one sensor element may itself be configured as or used as a passive guard. In this last case, one sensor element serves as a guard element for another sensor element.

In a further embodiment of the invention, the guard is a guard electrode, which serves to improve the measurement in the case of an impedance measurement and to largely block out undesired regions from the volume region monitored by the at least two measuring electrodes. By way of an appropriate geometric construction, the measurement region of these two electrodes can be configured in such a way that these electrodes have a measurement region in which each differs from the other in terms of measurement depth. As a result of the arithmetic-logic unit evaluating the impedance of the guard electrode, the guard electrode can take on the role of the second measuring electrode for the second measurement.

In a further embodiment of the invention, the measuring instrument is a limit level measuring instrument, which is configured to detect one of the states "covered by medium" and "not covered by medium". A limit level measuring instrument detects the level of the medium with respect to a comparison value. Depending on whether the level is above or below the predefined limit, the limit level measuring instrument emits a corresponding signal. For example, if the medium level has exceeded the highest permissible container level, the limit level measuring instrument emits the "limit level exceeded" signal to a central arithmetic-logic unit or a control room. For this purpose too, it is important to correctly detect the degree of covering of the sensor unit.

In a further embodiment of the invention, the measuring instrument is a fill level measuring instrument which is configured to detect the height of a filling material or the level of a fluid in a container. In this case, the measuring instrument can supply a numerical value, for example a fill level of a medium in a container, and not just the binary information "exceeded" or "not exceeded".

In a further embodiment of the invention, the physical medium property to be detected is at least one of the density of the medium and the permittivity of the medium. The density of a medium is defined by the ratio of a mass to the associated volume. The permittivity, also known as dielectric conductivity, specifies the permeability of a material to electric fields. For example, the relative permittivity of the medium may be of interest, which is the ratio of the permittivity of the medium to the general vacuum permittivity.

In a further embodiment of the invention, the sensor unit comprises two electrodes, the first electrode being used to take the first measurement and the second electrode being used to take the second measurement. Electrodes of this type are suitable in particular for impedance measurements, the impedance being the alternating current equivalent of the electrical resistance to direct current. In effect, impedance describes a resistance to alternating current, including phase information. However, other sensor elements may also be used, specifically ones which, due to the geometric dimensions or constructional configuration thereof, are suitable for taking measurements at different depths measured from the sensor surface in the medium.

In a further embodiment of the invention, the measuring instrument is configured as a vibration limit level measuring instrument. An instrument of this type generates vibrations in an actuator. The emitted oscillations subsequently propagate through the locally present media and are for example returned by a reflector. Subsequently, a sensor detects the transit time taken. To counteract the problems associated with media adhering in part, two reflectors may also be provided at different distances. Particular values have to be known to the sensor electronics, such as the distance from the oscillation source to the sensor via the reflector. For example, assuming a constant covering thickness, the covering thickness can thus be determined.

In a further embodiment of the invention, the first electrode and the second electrode are arranged rotationally symmetrically on the sensor unit and are both enclosed by an insulating layer.

A further aspect of the invention relates to a method for detecting media, comprising the steps of:
 taking at least two measurements at at least two different penetration depths in the medium using a sensor unit, and
 deciding whether the sensor unit is completely covered by a medium or parts of the medium are adhering to the sensor unit.

In a further embodiment of the invention, the disclosed method further comprises the step of:
 determining one or more physical substance properties of the medium using the arithmetic-logic unit.

A further aspect of the invention specifies a program element which, when executed on the arithmetic-logic unit, instructs the measuring instrument to carry out the disclosed method.

A further aspect of the invention specifies a computer-readable medium on which the program element is stored.

In the following, embodiments of the invention are disclosed with reference to the drawings. In the drawings, like reference signs denote like or similar elements. However, like or similar elements can also be denoted by different reference signs.

DETAILED DESCRIPTION OF EMBODIMENTS

The drawings are schematic and not to scale.

Figure 1:
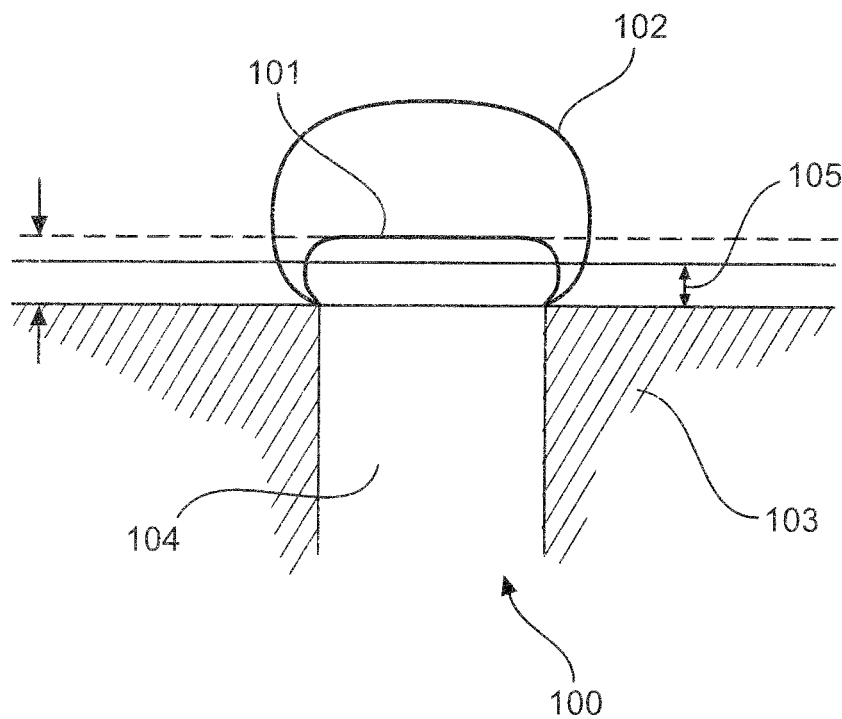
FIG. 1 shows a measuring instrument and two measurement regions at different depths in accordance with an embodiment of the invention.

FIG. 1 shows an embodiment of a measuring instrument 100 for detecting media, in particular a limit level measuring instrument, comprising a sensor unit 104. This measuring instrument 100 is configured to make a switching decision, which is largely independent of the value of the physical substance property and remains constant, as to whether the limit level has been reached, without any user input regarding the physical substance properties being required. This switching decision is thus merely dependent on the pre-established covering thickness 105. This is achieved in that the sensor 104 installed in the container 103 takes at least two measurements (the measurements may be separated for example in time or in space). The first measurement evaluates a region 101 close to the surface and the second evaluates a volume region 102 extending further into the depth.

Figure 2:
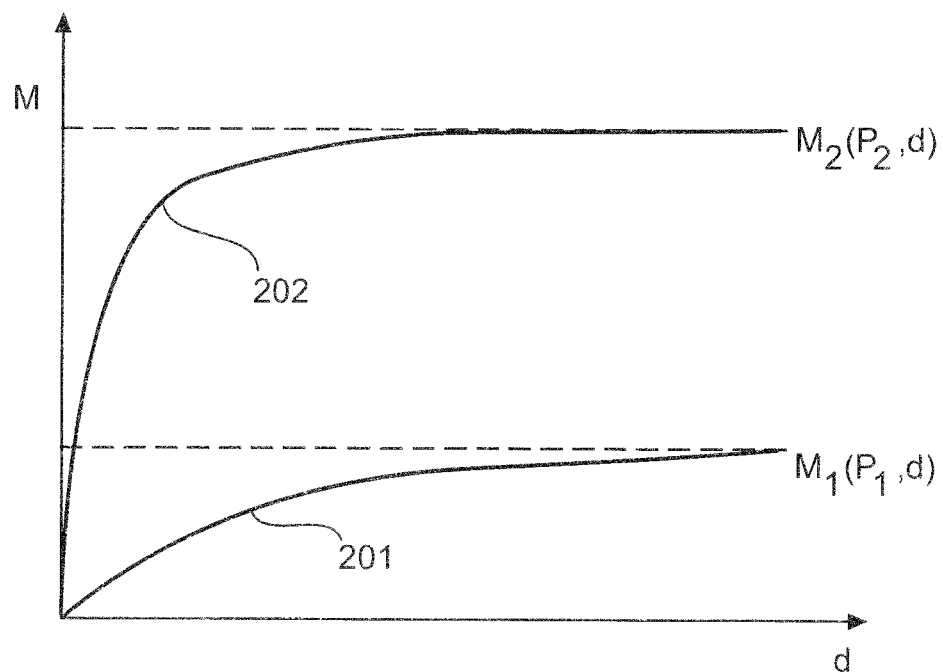
FIG. 2 shows two different measurement curves in accordance with a further embodiment of the invention.

FIG. 2 shows two different measurement curves which are obtained at the same covering thickness for different substance properties. However, curves of this type in principle also differ at different covering thickness for constant substance properties. This can also be represented in an equation system having two unknowns. Thus, to solve this equation system, at least two non-equivalent equations are required, and thus two measurements which are substituted into these equations. The measurement value $M_i(P_i, d)$ of a measurement is thus dependent both on the initially unknown value of the physical substance property $P_i$, which is to be measured, and on the thickness d to which the sensor is covered by the medium. Depending on how pronounced the physical substance property of the medium is, the curve shown may progress more steeply and to higher end values, or less steeply and to lower end values, with covering thickness. In addition, the curve progression may also be dependent on the nature of the detected physical substance property, for example the permittivity or the substance density. Also, the maximum possible measurement value in a medium when the sensor is completely covered by medium may vary with the nature of the detected physical substance property. Therefore, as a result of this dependency, neither $P_i$ nor d can be determined from a single measurement, since the underlying equation system is underdetermined. If two measurements having results $M_1(P_1, d)$ 201 and $M_2(P_2, d)$ 202 are taken and both measurements determine the same physical substance property $P_1=P_2$, the equation system has a unique solution and it is possible to determine $P_1$ and d, assuming that the volumes $V_i$ 101 and 102 detected by the sensor differ in depth. Measurement 1 in volume $V_1$ gives the result $M_1(P_1, d)$ and measurement 2 in volume $V_2$ gives results $M_2(P_2, d)$. More precisely, this means that one measurement is sensitive in the region close to the surface in volume $V_1$ 101 and the other is sensitive in a volume region $V_2$ 102 extending further into the depth. Close to the surface means that there is a limit distance $d_g$ of the thickness to which the sensor is covered at which the region of the sensor close to the surface no longer exhibits a change in measurement value when the covering thickness increases, and this limit distance is less than that of the second element. In this context, the volume $V_2$ may include the volume $V_1$. Furthermore, the transition between the region $V_1$ close to the surface and the volume-sensitive region $V_2$ may, depending on the measuring principle used, be continuous or abrupt, according to the measuring principle used. For detection of the covering by a medium or for evaluating whether a limit level is reached, the relative comparison of the two measurements may be sufficient, and explicit absolute calculation of P and d may not be required. By contrast, if the two measurements are sensitive to two different physical parameters $P_1 \neq P_2$ (for example relative permittivity and density), the equation to be solved is generally still underdetermined, since there is no generally valid relationship between physical medium properties (for example between relative permittivity and density or viscosity). The measuring principle used may for example be impedance measurement using two electrodes as a function of frequency (impedance spectroscopy). However, other measuring principles may also be used, for example vibration measurements.

Figure 3:
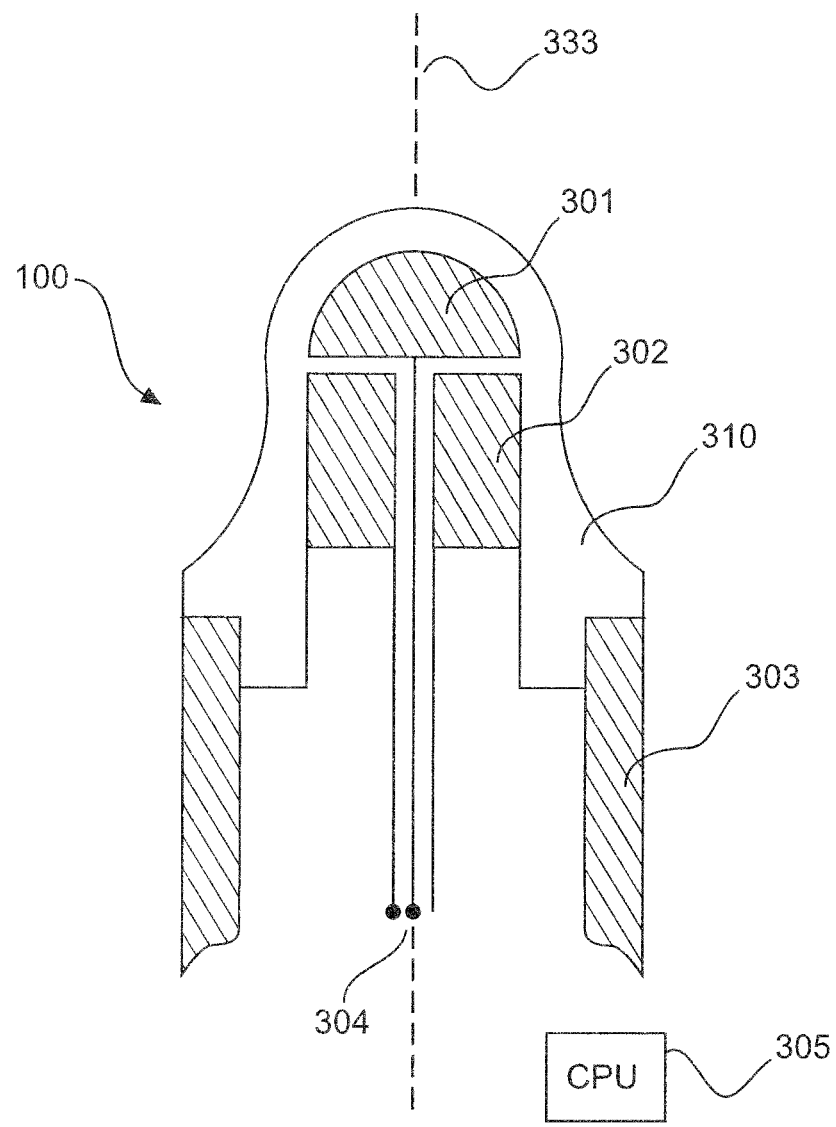
FIG. 3 shows a measuring instrument comprising electrodes and an insulating layer in a housing in accordance with a further embodiment of the invention.

FIG. 3 shows a further embodiment of a measuring instrument 100 for detecting media, in particular for detecting the covering of the sensor by filling material. Furthermore, substance properties of the filling material can also be determined, such as the permittivity (or the density). In this example, the impedance of the electrodes 301, 302 is preferably measured in the frequency range 10-400 MHz. The electrodes 301, 302 are connected to a power supply via the terminal 304. The electrodes 301, 302 are further enclosed by an insulating layer 310, for example made of polyetheretherketone or polytetrafluoroethylene, relative to the ground potential of the housing 303 or container wall 103. In this example, the passive guard is a guard electrode, the electrode 302 being used for this purpose. If the two electrodes 301, 302 have the same polarity, the guard electrode 302 prevents the formation of field lines of the electrode 301 close to the surface with respect to the housing 303. The volume detected by the electrode 301 by impedance spectroscopy thus goes much deeper into the medium than the volume detected by the electrode 302. Although a purely passive guard electrode already greatly minimises the effect of the adhesion, active evaluation of the impedance of the guard electrode in the form of a second measurement may bring about considerable advantages in the case of massive adhesions in the region of the measuring electrode. By comparing the two impedance measurements of the two electrodes, the relative permittivity of the medium can be determined at least relatively, and a switching point, largely independent of the value of the physical substance property of the medium, for a limit level sensor can thus be specified. This switching point is thus merely dependent on a covering thickness set in the sensor. The sensor head shown is rotationally symmetrical about the axis 333. However, the geometric formation of the two electrodes 301, 302 and of the reference element is largely irrelevant to the embodiment. All that matters is that the medium to be measured affects the impedance between the electrodes 301, 302 and the ground potential, and the volumes detected by the electrodes differ in depth. Calculations are performed by the arithmetic-logic unit 305. The decision as regards the switching point of a limit sensor is made in the arithmetic-logic unit 305.

Figure 4:
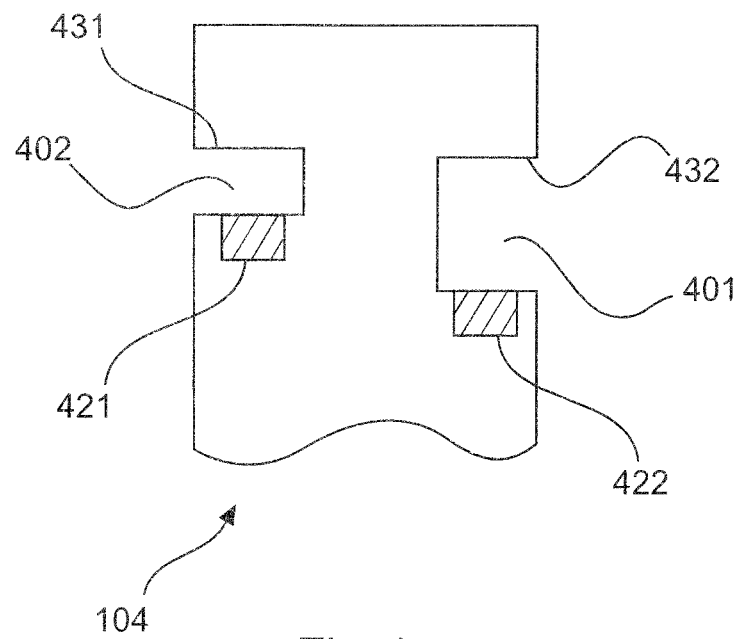
FIG. 4 shows a sensor unit having ultrasound measurement for detecting sound transit times in accordance with a further embodiment of the invention.

FIG. 4 shows an example of a measuring principle using sound sensors. In this case, the sensor unit 104 comprises combined sound sources and receivers 421, 422. These can, for example by way of an actuator, generate vibrations which are subsequently returned at a first reflector 431 and at a second reflector 432. In this example, the path "sound source 421—reflector 431—sensor 421" is shorter than the path "sound source 422—reflector 432—sensor 422". This results in different transit times from the source to the relevant sensor via the relevant reflector. If there were no adhesion of parts of the medium to the sensors 421 and 422, a single measurement from the sound sources 421 and 422 to a single sensor 422 via a single reflector 432 would be sufficient to determine the speed of sound in the medium in which the gap 401 is immersed. However, if the sensor unit 104 is only covered by the medium in part, two different media are to be found in the gaps 401, 402. In this case, the two different measurements make it possible, for example in the event of the same adhering layer thickness, to determine the speed of sound in the adhering medium, and in some cases also the layer thickness.

Figure 5:
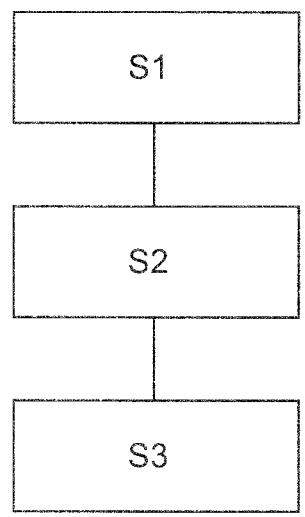
FIG. 5 shows a method for detecting media in accordance with a further embodiment of the invention.

FIG. 5 shows an exemplary method comprising the steps of:
taking (S1) at least two measurements at different penetration depths in the medium using a sensor unit 104. For example, capacitive measurements are taken at two different depths in the medium by two electrodes arranged in different positions. The electrodes may also be enclosed by an insulating layer 310.
deciding (S2) whether the sensor unit 104 is completely covered by a medium or whether parts of the medium are adhering to the sensor unit 104. For example, an equation system having two unknowns is solved. Unknown parameters are for example the permittivity and the thickness to which the sensor unit 104 is covered. For this purpose, for example, the unknown substance property may initially be eliminated, whereupon the layer thickness is calculated.
determining (S3) physical substance properties of the medium using the arithmetic-logic unit. After the layer thickness is calculated, the second unknown parameter, the at least one physical substance property, can also be determined.

For completeness, it should be noted that "comprising" and "having" do not exclude the possibility of other elements or steps and "a" or "an" does not exclude the possibility of a plurality. Further, it should be noted that features of steps which have been disclosed with reference to one of the above embodiments may also be used in combination with other features of steps of other above-disclosed embodiments. Reference signs in the claims should not be considered limiting.

LIST OF REFERENCE SIGNS

100 Measuring instrument
101 Region close to the surface
102 Volume region extending further
103 Container
104 Sensor unit
105 Covering thickness
201 Measurement
202 Measurement
301 Electrode
302 Electrode
303 Housing
304 Power supply
305 Arithmetic-logic unit
310 Insulating layer
333 Axis
401 Sensor-reflector distance
402 Sensor-reflector distance
421 Ultrasound transmitter/receiver
422 Ultrasound transmitter/receiver
431 Reflector
432 Reflector
S1 Taking measurement
S2 Deciding
S3 Determining

The invention claimed is:
1. A measuring instrument for detecting a fill level or a limit level of a medium, comprising:
a sensor unit configured to take two measurements at two different penetration depths in the medium, the two different penetration depths being relative to a position on the sensor unit, and an arithmetic-logic unit configured to distinguish complete covering of the sensor unit by a medium from adhesion of parts of the medium to the sensor unit, using the results of the at least two measurements.

2. The measuring unit according to claim 1, wherein the arithmetic-logic unit is further configured to determine a physical substance property of the medium by evaluating the at least two measurements.

3. The measuring instrument according to claim 1, further comprising:
   a passive guard configured to actively evaluate the influence of the covering and/or adhering medium.

4. The measuring instrument according to claim 1, wherein the sensor unit comprises two sensor elements, and wherein the measuring instrument further comprises:
   a passive guard is configured to largely limit the volume measured by the at least two sensor elements to the region in front of the sensor surface.

5. The measuring instrument according to claim 3, wherein the passive guard is a guard electrode.

6. The measuring instrument according to claim 1, wherein the measuring instrument is a limit level measuring instrument configured to determine one of the states "covered by medium" and "not covered by medium".

7. The measuring instrument according to claim 1, wherein the measuring instrument is a fill level measuring instrument is configured to detect the height of a filling material or the level of a fluid in a container.

8. The measuring instrument according to claim 2, wherein the physical medium property to be detected is the density or the relative permittivity of the medium.

9. The measuring instrument according to claim 1, wherein the sensor unit comprises two electrodes, and wherein the first electrode is configured to take the first measurement and the second electrode is configured to take the second measurement.

10. The measuring instrument according to claim 1, wherein the sensor unit is configured to take a measurement of the impedance of the electrodes.

11. The measuring instrument according to claim 9, wherein the first electrode and the second electrode are arranged rotationally symmetrically on the sensor unit, and wherein the first electrode and the second electrode are enclosed by an insulating layer.

12. The measuring instrument according to claim 1, wherein the sensor unit is configured as a vibration limit level measuring instrument.

13. A method for detecting a fill level or limit level of a medium, comprising:
   taking at least two measurements at at least two different penetration depths in the medium using a sensor unit, the two different penetration depths being relative to a position on the sensor unit, and
   deciding whether the sensor unit is completely covered by a medium or parts of the medium are adhering to the sensor unit.

14. The method according to claim 13, further comprising the step of:
   determining at least one physical substance properties of the medium using an arithmetic-logic unit.

15. A program element which, when executed on an arithmetic-logic unit of a measuring instrument, instructs the measuring instrument to carry out the method according to claim 13.

16. A computer-readable medium on which a program element is stored, wherein when the program element is executed on an arithmetic-logic unit of a measuring instrument, instructs the measuring instrument to carry out the method according to claim 13.

* * * * *